United States Patent [19]

Nashef

[11] Patent Number: 4,770,665
[45] Date of Patent: * Sep. 13, 1988

[54] ELASTOMERIC POLYMER INCORPORATION INTO IMPLANTABLE BIOLOGICAL TISSUE TO INHIBIT CALCIFICATION

[75] Inventor: Aws S. Nashef, Costa Mesa, Calif.

[73] Assignee: American Hospital Supply Corporation, Deerfield, Ill.

[ * ] Notice: The portion of the term of this patent subsequent to Nov. 6, 2001 has been disclaimed.

[21] Appl. No.: 795,125

[22] Filed: Nov. 5, 1985

[51] Int. Cl.$^4$ .................. A61L 17/00; A63B 51/02; D01C 3/00; D01F 5/00
[52] U.S. Cl. .................................. 8/94.11; 623/1; 623/2; 623/3; 8/94.21
[58] Field of Search ............... 8/94.11, 94.21; 3/1, 3/1.4, 1.5; 623/1, 2, 3

[56] References Cited

U.S. PATENT DOCUMENTS

| 4,066,583 | 1/1978 | Spaulding | 260/17.4 |
|---|---|---|---|
| 4,120,649 | 10/1978 | Schechter | 8/94.11 |
| 4,182,750 | 1/1980 | Sullivan et al. | 424/1 |
| 4,314,800 | 2/1982 | Monsheimer et al. | 8/94.1 R |
| 4,323,358 | 4/1982 | Lentz et al. | 8/94.11 |
| 4,350,806 | 9/1982 | Wagener | 528/280 |
| 4,369,036 | 1/1983 | Saito et al. | 8/115.5 |
| 4,377,010 | 3/1983 | Fydelor et al. | 623/1 |
| 4,378,224 | 3/1983 | Nimni et al. | 8/94.11 |
| 4,383,832 | 5/1983 | Fraefel et al. | 8/94.11 |
| 4,402,697 | 9/1983 | Pollock et al. | 8/94.11 |
| 4,481,009 | 11/1984 | Nashef | 8/94.11 |
| 4,511,478 | 4/1985 | Nowinski et al. | 210/691 |

OTHER PUBLICATIONS

Brauer, G. M. and D. J. Termini, *J. of Applied Polymer Sci.*, vol. 17, pp. 2557-2568 (1973).

Ratner, B. D. and A. S. Hoffman, "Synthetic Hydrogels for Biomedical Applications", in *Hydrogels for Med. and Related Applications*, J. Andrade, Ed., ACS Symposium Series, 31, pp. 1-36 (1976).

Lloyd D. and C. Burns, *J. of Polymer Science: Polymer Chem. Edition*, vol. 17, pp. 3473-3483 (1979).

Primary Examiner—Paul Lieberman
Assistant Examiner—John F. McNally
Attorney, Agent, or Firm—Bernard, Rothwell & Brown

[57] ABSTRACT

A process for the preparation of implantable biological tissue wherein elastomeric copolymers are incorporated into the tissue in an amount sufficient to increase the durability of the tissue as well as to reduce calcification of the tissue upon implantation. Mitigaton of calcification is retained when the tissue is subjected to flexing, stretching, or similar motion.

35 Claims, No Drawings

ELASTOMERIC POLYMER INCORPORATION INTO IMPLANTABLE BIOLOGICAL TISSUE TO INHIBIT CALCIFICATION

BACKGROUND OF THE INVENTION

With the introduction of glutaraldehyde preservation of biological tissue, and in particular, porcine bioprosthetic heart valves, it has been possible to: (a) overcome the poor performance of early formaldehyde-preserved implanted tissue valves; (b) discontinue the use of homograft valves; and (c) avoid the undesirable use of anticoagulants required to prevent thromboembolism associated with the use of non-bioprosthetic (mechanical) heart valves especially in children. Although the relatively biologically inert glutaraldehyde-preserved valves of Carpentier and others have demonstrated excellent long-term durability in most instances, serious drawbacks such as tissue-fatigue and a propensity toward calcification have plagued their continued use. Moreover, it was initially contemplated that children and adolescents would be among those deriving the greatest benefit from the glutaraldehyde-preserved bioprosthetic heart valves since the anticoagulants required with mechanical prostheses could be eliminated. Results from an increasing number of recent clinical studies, however, indicate that severe calcification of these tissues with relatively short-term failure is prevalent among children and adolescents. Thus, despite their long-term durability and overall reduced incidence of complications, these glutaraldehyde-preserved valves have been deemed by some to be unsuitable for use in children.

Calcification of tissue remains a mystery for the most part; however, various factors including calcium metabolism diseases, age, diet, degeneration of tissue components such as collagen, and turbulance have previously been shown to be involved to a certain extent. Recently, the occurrence of a specific calcium-binding amino acid, laid down after implantation of glutaraldehyde-preserved porcine xenografts, has been demonstrated; and it has been postulated to play a role in calcification. While calcification has been accompanied by degradative changes in the glutaralde-hydetreated collagen fibers of the implanted tissue, it remains unclear whether the dystrophic calcification is a cause or the result of tissue degradation. Nevertheless, there has been a continued effort to elucidate the source of the calcification problem with implanted tissue, with the hope that a remedy will be soon to follow.

One method of inhibiting the intrinsic calcification of biological tissues is to incorporate a polymer into the implantable tissue, as described in U.S. Pat. No. 4,481,009, herein incorporated by reference. One embodiment of this method involves covalently bonding to the tissue a monomer capable of further polymerization. This tissue is then contacted with a second monomer under polymerization conditions such that a tissue-bonded polymer is formed in situ.

While this method of mitigating calcification is suitable for certain applications, not all polymers impart an elastomeric property to the tissue. Such an elastomeric property may be desirable in tissues which will be subjected to stretching or flexing once implanted. Tissues which will be repeatedly stretched or flexed after implantation include, among others, those implanted to form part or all of a diaphragm, heart valve, other portions of an artificial heart, or a bladder. It has been found that when certain relatively non-elastomeric polymers are bound to biological tissue that is subsequently subjected to repeated flexing, the polymer's ability to mitigate calcification of the tissue may be lost. For example, tissue into which a relatively non-elastomeric polymer was incorporated according to the method of U.S. Pat. No. 4,481,009, in which the first monomer solution comprised acrylic acid, and the only monomer in the second monomer solution was acrylamide, became calcified after being subjected to mechanical flexing and then implanted. The non-elastomeric polymer was found to have cracked when repeatedly flexed. Thus, there exists a need for a method of treating implantable biological tissue to inhibit calcification so that the inhibition of calcification is retained in tissues subjected to flexing, stretching, and similar movement after implantation.

SUMMARY OF THE INVENTION

In accordance with the present invention, a process for treating animal biological tissue prior to implantation into an animal involves fixing the tissue under tissue-fixing conditions; contacting the tissue with a first solution of one or more monomers capable of further polymerization under conditions sufficient to covalently bond said monomer(s) to the tissue; and contacting the tissue with a second solution comprising one or more monomers or oligomers under polymerization conditions such that the monomers or oligomers in the second solution react with said covalently-bound first monomer(s) to form a tissue-bound elastomeric polymer. The elastomeric polymer inhibits calcification and improves the durability and flexibility of the tissue as compared to tissues treated with more rigid polymers Mitigation of calcification is retained in tissues having an elastomeric polymer incorporated therein which are subjected to stretching, flexing, and other such motion, as well as those which are not subjected to such motions.

DETAILED DESCRIPTION OF THE INVENTION

In accordance with the present invention, various elastomeric polymers are incorporated into the biological tissue. The thus-treated biological tissues have been found to have increased durability and flexibility and improved retention of calcification inhibition when subjected to stretching or flexing, over tissues treated with less elastomeric polymers, and thus are particularly suited for flexible or moveable applications, such as bioprosthetic heart valves.

The implantable biological tissues which can be treated by the present invention can be derived from a number of animal sources including, inter alia, bovine, porcine, horse, sheep, kangaroo, rabbit or human cadaver. The animal parts which are generally utilized from such sources include tendons, ligaments, bladders, heart valves, dura mater, fascia lata, amnion, collagen or pericardium. Tissue used for augmentation, such as skin patches, pericardial patches, aortic patches, and tympanic membranes, may also be utilized.

The polymers which are incorporated into the biological tissue are any polymers which are elastomeric, biocompatible, and durable. As used herein, "elastomeric" polymers are those which are sufficiently flexible to retain calcification inhibition properties when the tissue into which they are incorporated is subjected to flexing, stretching, or other such motions. The polymer should also be flexible enough for the tissue to be functional once implanted. For example, tissue implanted as a bladder should be sufficiently flexible to expand and contract. Thus, the degree of flexibility required will vary somewhat according to the purpose (i.e., body part) for which the tissue is to be implanted. The desired degree of durability will likewise vary with the purpose for which the tissue is to be implanted. The implanted tissue should be sufficiently durable to function for extended periods of time.

The term "biocompatible polymers" is used in the art to describe polymers suitable for introduction into living tissues or other portions of a patient's body, e.g., the bloodstream. Such polymers ideally are hydrophilic, relatively non-thrombogenic, non-toxic, and non-antigenic, and do not cause problematic tissue necrosis or irritation, or erythrocyte lysis.

Many suitable polymers are known in the art. Examples of flexible, biocompatible polymers are found in U.S. Pat. Nos. 4,350,806 and 4,377,010. In U.S. Pat. No. 4,377,010, implantable copolymers suitable for surgical use are prepared by graft-polymerizing an ethylenic carboxylic acid onto various commercially available polymer films. The degree of flexibility in the resulting copolymer is said to increase with the degree of grafting. If the ethylenic carboxylic acid polymerizes with the "base polymer" (the film) throughout the film's entire thickness, the resulting copolymer is more flexible than if the grafting were limited to the base polymer's surface. The preferred ethylenic carboxylic acids used in this graft-polymerization process are acrylic acid or methacrylic acid. The base polymer comprises one or more polymers selected from polyolefins, partially or fully fluorinated polyolefins, polyethylene glycolterephthalates, polyamides, polyacrylonitriles, cellulosic based polymers, polyvinylchlorides, polyvinylidenechlorides, polyvinylalcohols, polyethyleneglycols, polyvinylpyrrolidones and mixtures thereof. Preferably, the base polymer is selected from partially and fully fluorinated olefins, especially polyethylene, polypropylene, and polytetrafluoroethylene and most preferably a polyetherurethane.

In U.S. Pat. No. 4,350,806, segmented thermoplastic copolyesters useful as biomedical materials comprise long-chain ester units joined through ester linkages to short-chain ester units. The long-chain ester units are preferably polyethers incorporating at least one thermally stable heterocyclic ring per molecule and may be, for example, hydantoin polyethers such as hydantoin polyethylene. The short chain unit is preferably chosen from polyethylene terephthalate, 1,4-cyclohexanedimethylol terephthalate, or polybutylene terephthalate.

Other suitable biocompatible and elastomeric polymeric materials which may be incorporated into the biological tissue by the procedures described below include styrene-butadiene copolymers; acrylonitrile-butadiene copolymers (e.g., methacrylonitrile-isoprene copolymers); olefin elastomers (e.g., ethylene-propylene copolymers or polyethylene); butyl rubber compounds (e.g., isobutylene-isoprene or isobutylene); and silicon rubber compounds. Other polymers which may be employed in the method of the invention include, but are not limited to, ethylene-vinyl acetate copolymers, polyvinyl-pyrrolidone, polyetherurethane, polyester-polyether block copolymers, methacrylate-styrene copolymers, polymethacrylates, acrylate-diolefin copolymers, methyl methacrylate-butadiene-styrene copolymers, and many others.

One skilled in the art will therefore recognize the many different combinations of monomers which may be included in the first and second monomer solutions in the process of the invention to incorporate into the biological tissue polymers having the desired biocompatibility, flexibility, and durability. Certain relatively non-elastomeric monomers, such as acrylamide, may be included, since copolymers comprising non-elastomeric monomers together with elastomeric monomers may yield an elastomeric copolymer. By controlling the relative proportions of such monomers, the desired degree of elasticity may be achieved.

When covalent bonding of the polymer to the biological tissue is desired, the monomers advantageously have certain structural characteristics. The monomers in the first solution should have reactive chemical groups that allow covalent bonding to the biological tissue (through reactive groups on the tissue), either directly or through a linking compound (described below). The monomers in the first solution also are reactive with the monomers or oligomers in the second solution such that, upon addition of the second solution, the tissue-bound polymer is formed in situ. A variety of reactive groups are contemplated, depending upon the nature of the elastomeric polymer to be formed. For example, preferred monomers are those which are capable of having free radicals generated, by conventional means, at a position that allows subsequent polymerization with the monomers and/or oligomers in the second solution through reactive double bonds. Examples of other reactive monomers are those having free amine or hydroxyl groups, which can react with monomers or oligomers having isocyanate groups (to form urea urethane or urethane linkages), carboxylic acids, acid chlorides or anhydrides (to form amide, imide or ester linkages), and the like.

In one embodiment of the invention, the first monomer solution contains one or more monomers (preferably just one monomer species) chosen from acrylic acid, methacrylic acid, acrylamide, methacrylamide, esters of acrylic acid, or esters of methacrylic acid, with acrylic acid being preferred. The second solution comprises one or more monomers, at least one of which is an ester of acrylic acid or of methacrylic acid. If the second solution contains only one monomer species, it is preferably an ester of methacrylic acid.

When there is a mixture of monomers in the second monomer or oligomer solution, a random elastomeric copolymer is generally formed. If desired, a mixture of oligomers can be employed in the second monomer or oligomer solution to produce a block copolymer. If a mixture of oligomers is employed, the oligomers are generally short enough in chain length that they can diffuse freely through the interstices of the biological material. The chain length generally ranges from about 5 to 50 monomers, preferably about 10 to 20. Such oligomers are preferably vinyl terminated so that they can further polymerize after being contacted with the first monomer.

In the case of an acrylic or methacrylic ester copolymer, the copolymer can contain a wide variety of weight percentages of the unit(s) derived from an ester of acrylic or methacrylic acid. The proportion of the total copolymer derived from esters of acrylic or methacrylic acid should be such that the tissue exhibits the desired degree of flexibility. With increasing levels of the ester(s) of acrylic or methacrylic acid, the polymer's flexibility increases. Increasing levels of more rigid polymers, such as polyacrylamide, decreases the flexibility of the biological material. Thus, by controlling the ratio of the polymeric components, one can tailor the tissue to whatever degree of flexibility and durability is desired. The ester(s) of acrylic or methacrylic acid generally constitute from about 30 to about 100 weight percent of the total weight, preferably from about 50 to about 100 weight percent of the total weight of the polymers in the second solution.

In accordance with the present invention, after extraction of the tissue from the animal source, it is initially stored and is fixed within a tissue-stabilizing pH range; that is, within a pH range that is not deleterious to the tissue components. A preferred pH range is from about 7.0 to about 7.6, and a more preferred pH range is from about 7.1 to about 7.4. The most preferred pH in accordance with the present invention is 7.3. As used herein, the term "fixed" or "fixed tissue" refers to tissue which has been treated with a tanning solution, such as 4 percent formaldehyde or aqueous solutions of glutaraldehyde, typically 0.1 percent to 5 percent by weight, for a period of time and under conditions conventionaly used to prepare natural tissue for implantation. Fixing biological tissue with such tanning agents as glutaraldehyde is known to cross-link proteins in the tissue, thus rendering the tissue substantially non-antigenic so it may be implanted in an animal different from the donor animal.

Buffers used in accordance with the present invention are preferably stable and do not interfere with the stabilization process. Such buffers have a buffering capacity sufficient to maintain an acceptable pH, particularly during the fixation of the tissue. The choice of the appropriate buffer, and its concentration will depend upon specific tissue preparation conditions; variations of which have been introduced by several manufacturers. The buffer can be either conventional 0.01–0.02M phosphate-buffered saline (PBS) or phosphate-deficient solutions such as those containing less phosphate than these 0.01 to 0.02M PBS solutions, and preferably less than about 0.001 to about 0.002M phosphate. Preferred buffers in accordance with the present invention include borate, carbonate, bicarbonate, cacodylate (found to be non-toxic in animals), and other synthetic, artificial, or organic buffers such as N-2-hydroxyethylpiperazine-N'-2-ethanesulphonic acid (HEPES); morpholine propanesulphonic acid (MOPS); and 1,4-piperazinediethanesulphonic acid (PIPES). Tissue prepared in HEPES buffer advantageously results in a significant reduction of calcification after implantation, and is therefore most preferred in the present invention. Preferably, the buffered or unbuffered solutions used in accordance with the present invention should not interfere with the tissue-stabilizing process afforded by the fixing agents such as glutaraldehyde. That is, they should not react with the fixing agent or prevent the fixing agent from achieving proper fixation of the tissue. Illustrative of these unsuitable buffers are those containing primary and secondary amines such as tris(hydroxymethyl)aminomethane (Tris), which are known to react with the aldehyde groups of glutaraldehyde and thus interfere with the normal tissue stabilization process.

The polymeric material can either be impregnated into the biological tissue by inclusion within the interstices of the tissue to form a physical or mechanical bond or it can be chemically bonded thereto. Covalent bonding has the advantage that the polymeric material will not be displaced from the tissue after implantation nor be subject to dislocation of layers within the tissue and is thus the preferred technique. A number of functional chemical groups suitable for covalent bonding are present in the proteins of the biological tissue and include $\alpha$- and $\epsilon$-amino groups; $\alpha$-, $\beta$-, and $\gamma$-carboxyl groups; the sulfhydryl and hydroxy groups of cysteine and serine; the imidazole group of histidine; and the phenol ring of tyrosine. In some cases, the "fixing" process may have cross-linked the amino groups of the tissue, so that they are not available for covalent bonding. The mucopolysaccharides of biological tissue have free carboxyl groups on which a variety of monomers can be attached. In a preferred embodiment, a monomer in the first solution is covalently bonded to the biological tissue through direct bonding or through linking compounds ("spacers"). Examples of various spacers or coupling agents useful as linking compounds include diamines which are used to bond the free carboxyl residues on the protein and mucopolysaccharide components of the tissue. Preferably, an activating factor such as a carbodiimide is used with the diamines. The carbodiimide activating factor is preferably water-soluble. A suitable activating factor is 1-ethyl-3(3-dimethylaminopropyl)carbodiimide-HCl. Examples of this type of coupling are illustrated by Lloyd and Burns in Journal of Polymer Science: Polymer Chemistry Edition, Vol. 17, pp. 3459–3483 (1979), incorporated herein by reference. Preferred diamines in accordance with the present invention include those having the formula $R-(NH_2)_2$ wherein R is an aliphatic group having straight, branched, or cyclic chain; or an aromatic group. It is contemplated that the chain length or bulkiness of the R groups should be such that the diamine can freely diffuse within the protein network of the tissue. Preferably, the diamine should be water-soluble. The most preferred diamine in accordance with the present invention is ethylenediamine.

In accordance with the present invention, the fixed tissue is contacted with a first solution of a monomer which is capable of subsequent polymerization with the second solution of monomers or oligomers. In the alternative, the fixed tissue can be contacted with the spacer or linking compound, described above, rinsed, and then subsequently contacted with the first monomer solution. When a diamine spacer is used, the monomers are covalently bonded to the free amino group of the diamine spacer compound which was previously bound to the tissue as described above. Examples of the type of monomers which may be in this first solution include acrylic acid, methacrylic acid, acrylamide or methacrylamide, esters of acrylic acid or esters of methacrylic acid. After the tissue has been contacted with this first solution of monomer, the tissue is thoroughly rinsed in order to remove any non-covalently bonded monomer trapped within the tissue. By removing non-covalently bonded monomers one avoids any subsequent polymerization of these monomers with the additional monomers that are subsequently contacted with the tissue.

The procedure for exposing the tissue to the second solution of monomers or oligomers will depend upon the structure of the monomer covalently attached to the tissue and the nature of the polymer being formed. For example, if the covalently attached first monomer has reactive groups, such as amino, hydroxyl, carboxylic and the like, the second solution of reactive monomers or oligomers can be contacted directly with the tissue.

If the covalently attached monomer is an ethylenically unsaturated compound, the tissue is advantageously exposed to a free radical initiator. Many types of free-radical initiators (or polymerization initiators) are known in the art, including ionizing radiation, ultraviolet radiation, thermal radical initiators, redox polymerization initiators, chemicals such as certain peroxides or persulfates, etc. Any suitable conventional initiators can be used including aqueous solutions of ammonium persulfate containing minor amounts of N,N,N',N'-tetramethylenediamine. The free radical initiator is employed in an amount which catalyzes the reaction of the covalently-bound monomer with monomers or oligomers added subsequently and initiates polymerization of the monomers. The tissue is then contacted with a second solution of monomers or oligomers. In one embodiment of the invention, this solution contains two or more different monomers or oligomers of acrylic or methacrylic acid or derivatives thereof, at least one of which is an ester derivative. Examples of the ester of acrylic or methacrylic acid which can be used to form the copolymer include methacrylate, methyl methacrylate, ethyl acrylate, ethyl methacrylate, propyl acrylate, propyl methacrylate, butyl acrylate, butyl methacrylate, hydroxy ethyl acrylate, hydroxy ethyl methacrylate, hydroxy propyl acrylate, hydroxy propyl methacrylate, hydroxy butyl acrylate, hydroxyl butyl methacrylate, acrylic acid glycerine ester, methacrylic acid glycerine ester, acrylic acid erythritol ester, methacrylic acid erythritol ester, acrylic acid pentaerythritol ester, methacrylic acid pentaerythritol ester, or mixtures thereof. Preferred esters include the derivatives of methacrylic acid with ethyl methacrylate, butyl methacrylate and hydroxyethyl methacrylate being particularly preferred. The remaining monomers or oligomers in the solution can be acrylic acid, methacrylic acid, acrylamide, methacrylamide or mixtures thereof. When two or more esters of acrylic or methacrylic acid are used, the various combinations of ethyl methacrylate, butyl methacrylate and hydroxyethyl methacrylate are preferred The monomers or oligomers are suspended in the second solution in an amount ranging from about 0.1 to about 10 weight percent. Preferably, the solution contains from about 0.5 to about 6 weight percent of the monomers or oligomers, most preferably, from about 0.5 to about 2 weight percent total of monomers or oligomers.

In addition to the monomers or oligomers that are present in the second solution, conventional cross-linking agents are generally present in conventional amounts. One example of a cross-linking agent which has been found particularly suitable for use in the present invention is bisacrylamide. Generally, the cross-linking agent is present in amounts of from about 0.02 to about 2.5, preferably from about 0.1 to about 0.4, with about 0.25 weight percent being most preferred. The degree of cross-linking in the polymers can be controlled by the amount of cross-linking agent that is present.

Advantageously, a free-radical scavenger is included in the second monomer solution to minimize homopolymerization of the monomers in solution and to, quench the generated free-radicals on the tissue surface. Selective polymerization of the monomers in the second solution with those covalently-bound first monomers which are located in the interstices of the tissue is thus promoted, as described in the concurrently filed patent application U.S. Ser. No. 795,124. Several free-radical quenchers are known in the art, with ferrous ammonium sulfate being preferred for use in this invention. The free-radical quencher is generally present in from about 0.15 to about 0.4 weight percent, and preferably from about 0.2 to about 0.3 weight percent of the second monomer solution, most preferably about 0.25 weight percent.

After polymerization, the tissue is preferably rinsed, sterilized and rinsed again and is then ready for implantation. The tissue can be sterilized by any conventional means, including exposure to ethylene oxide or immersion in a solution containing glutaraldehyde or formaldehyde. A sterilizing solution containing 4–5% formaldehyde may contain additional substances such as ethanol, surfactants, and buffering compounds.

Advantageously, the tissue transfer steps above are conducted in an inert (e.g. nitrogen) atmosphere. The solutions which contact the tissue during and after the free-radical initiation step are advantageously purged with nitrogen prior to use.

The present invention is further illustrated by the following examples which are not intended to be limiting. It is to be understood by those skilled in the art that modifications and changes can be made thereto without departing from the spirit and scope of the invention.

EXAMPLE I

Bonding of a Relatively Non-Elastomeric Polymer in Biological Tissue

Extracted bovine pericardial tissue was thoroughly rinsed and shipped in an isotonic (285±15 milliosmols) solution containing 0.54 grams/liter of the sodium salt of HEPES and 0.885 weight percent sodium chloride at pH 7.3 at about 4° C.; and fixed with 0.625 weight percent glutaraldehyde in an isotonic solution containing 5.39 grams/liter of the sodium salt of HEPES, 0.440 weight percent sodium chloride, and 2.6 grams/liter of $MgCl_2 \cdot 6H_2O$ at room temperature.

Samples of the tissue (each sample weighing about 5 grams when wet) were then each immersed in a 40 ml solution containing about 2.5 grams of ethylenediamine at pH 4.75. After about 30 minutes, 2 grams of water-soluble 1-ethyl-3(3-dimethylaminopropyl) carbodiimide-HCl were added stepwise while the pH was maintained at 4.75 for a 30 minute incubation period at room temperature. The pH is preferably controlled to 4.75±0.1 in order to ensure maximum reactivity of the diamine with the carboxylate groups on the tissue. Next, the tissue was rinsed thoroughly with HEPES-buffered-saline at pH 7.4 and transferred into an aqueous solution containing 0.2M acrylic acid at pH 4.75 for about 30 minutes. The tissue was then thoroughly rinsed with HEPES-buffered-saline to remove any non-coupled acrylic acid from the tissue. The acrylic acid-coupled tissue was then further suspended in about 40 ml distilled water and bubbled with nitrogen for about 30 minutes before replacing with a 40 ml solution of 2 percent ammonium persulfate containing 0.6 percent (v/v) N,N,N',N'-tetramethylenediamine which had been previously bubbled with nitrogen for 30 minutes. After 30 minutes, the free radical initiation step was completed, and the tissue was transferred to 40 ml of a 1 weight percent acrylamide solution containing 0.25 weight percent bisacrylamide (N,N'-methylbisacrylamide) and 0.25 weight percent ferrous ammonium sulfate. All tissue transfer steps were performed in a nitrogen atmosphere. The reaction mixture was allowed to polymerize for about 60 minutes. The tissue samples having this relatively non-elastomeric polymer incorporated therein were then divided into three groups.

Tissue in the first group was rinsed with distilled water, sterilized in a solution containing 4 percent formaldehyde, rinsed again in sterile saline and implanted subcutaneously in growing rabbits. The tissue was retrieved up to six weeks later at regular one-week intervals; and the extent of tissue calcification was assessed by quantitatively monitoring the weight percent calcium in dried tissue using atomic absorption analysis, and histologically by visually monitoring the degree of calcification in Von Kossa-stained tissue sections.

The degree of calcification was compared with control tissue which was processed and fixed as above, then further sterilized in a solution containing about 4 percent formaldehyde, rinsed in sterile saline to remove residual glutaraldehyde at a time immediately prior to implantation, and implanted subcutaneously in growing rabbits. The control tissue had no polymer incorporated therein. Both the histologic and quantitative results indicated that the implanted tissue having acrylamide incorporated thereon effected a significant reduction in calcification compared to the control tissue. Table I shows a qualitative evaluation of the degree of calcification on a scale of 0, 1, 2 and 3 using Von Kossa stain, where "3" represents significant calcification, with higher values being possible.

A second group of tissue samples having the polymer incorporated therein were rinsed and sterilized as above and implanted as mitral valve replacements in the hearts of growing sheep. The tissue was therefore subjected to repeated flexing after implantation. Control tissue (lacking bonded polymer) was also implanted as mitral valve replacements. Twenty weeks after implantation, the implanted tissues were examined. Tissue having polymer bonded therein was found to have become calcified to a degree similar to that of the control tissue.

The third group of tissue samples having the polymer incorporated therein were placed on accelerated flexing machines (pulsatile) operated at 1900 rpm, and flexed for 120 million cycles (approximately equivalent to the flexing that tissue implanted in a human heart valve would undergo in 3 years). The tissue was then rinsed and sterilized as above and implanted subcutaneously in rabbits. Control tissue (lacking bonded polymer) was also implanted. Examination of the tissues showed that the tissue having polymer bonded therein became calcified at a rate similar to that of the control tissue. At 6 weeks post-implantation, the tissue having the polymer bonded therein showed a degree of calcification that was rated "4".

Thus, it can be seen that while calcification was mitigated in tissues having relatively non-elastomeric polymers bonded therein which were implanted in non-flexed situations, the reduction in calcification was lost in such tissues subjected to flexing.

EXAMPLE II

Bonding of an Elastomeric Polymer in Biological Tissue

Extracted bovine pericardial tissue was thoroughly rinsed and shipped in an isotonic (285±15 milliosmols) solution containing 0.54 grams/liter of the sodium salt of HEPES and 0.885 weight percent sodium chloride at pH 7.3 at about 4° C. The tissue was fixed with 0.625 weight percent glutaraldehyde in phosphate-buffered saline (PBS), and divided into five groups.

The first group of tissue samples were further sterilized in a solution of either 4 percent formaldehyde in PBS or a 4% formaldehyde/22.5% ethanol/1.2% Tween-80 TM solution buffered with HEPES, pH 7.4. The tissue was then rinsed in sterile saline to remove residual glutaraldehyde at a time immediately prior to implantation, and implanted subcutaneously in growing rabbits. This "control" tissue was retrieved from half the rabbits after 3 weeks, and from the remaining rabbits after 6 weeks.

After retrieval, the extent of tissue calcification was assessed by quantitatively monitoring the weight percent calcium in dried tissue using atomic absorption analysis; and histologically by visually monitoring the degree of calcification in Von Kossa-stained tissue sections.

The remaining four groups of tissue samples were treated according to the method of the invention to bond different elastomeric copolymers to the tissue. Five-gram (wet weight) samples of the fixed pericardial tissue were each immersed in a 40 ml solution containing about 2.5 grams of ethylenediamine at pH 4.75. After about 30 minutes, 2 grams of water-solution 1-ethyl-3(3-dimethylaminopropyl) carbodiimide-HCl was added stepwise while the pH was maintained at 4.75 for a 30 minute incubation period at room temperature. The pH is preferably controlled to 4.75±0.1 in order to ensure maximum reactivity of the diamine with the carboxylate group. Next, the tissue was rinsed thoroughly with HEPES-buffered-saline at pH 7.4 and transferred into an aqueous solution containing 0.2M acrylic acid at pH 4.75 for about 30 minutes. The tissue was then thoroughly rinsed with HEPES-buffered-saline to remove any non-coupled acrylic acid from the tissue. The acrylic acid-coupled tissue was then further suspended in about 40 ml distilled water and bubbled with nitrogen for about 30 minutes before replacing with a 40 ml solution of 2 percent ammonium persulfate containing 0.6 percent (v/v) N,N,N',N'-tetramethylenediamine which was previously bubbled with nitrogen for 30 minutes. After 30 minutes, the free radical initiation step was completed, and the tissue was transferred to 40 ml of a solution containing one of the following combinations of monomers. All solutions contained 0.5 weight percent of each monomer.

Copolymer A = acrylamide + ethyl methacrylate
Copolymer D = ethyl methacrylate + butyl methacrylate
Copolymer E = ethyl methacrylate + hydroxyethyl methacrylate
Copolymer F = butyl methacrylate + hydroxyethyl methacrylate Each solution also contained 0.25 percent bisacrylamide (N,N'-methyl bisacrylamide) and 0.25 percent ferrous ammonium sulfate. All tissue transfer steps were performed in a nitrogen atmosphere. The reaction mixtures were allowed to polymerize for about 60 minutes, and the tissue was then rinsed with distilled water.

Approximately half of the tissue samples in each of the four copolymer groups were then stored in a glutaraldehyde solution. The other half of the samples were placed on accelerated flexing machines (pulsatile) and flexed for 120 million cycles (approximately equivalent to the flexing that tissue implanted in a human heart valve would undergo in 3 years). All the samples were then rinsed in distilled water and sterilized in a solution of 4 percent foraldehyde in PBS or 4% formaldehyde/22.5% ethanol/1.2% Tween-80 ™ buffered with HEPES, pH 7.4. The samples were then rinsed in sterile saline, and implanted in growing rabbits. Half the samples in each test group were retrieved after 3 weeks and the rest after 6 weeks. The extent of calcification was assessed as in Example I above. The results for each test group and for the control tissue (above) are given in Table 2.

It is evident that calcification is effectively reduced in tissues having the elastomeric copolymers incorporated therein, when compared with the controls which lack polymers, and that this mitigation of calcification is retained when the tissue is subjected to flexing.

TABLE 1

Effect of Polymer-Incorporating Treatment of Pericardial Tissue on the Degree of Calcification in Growing Rabbits

| Implant Time (in weeks) | Treatment Polymer | Control |
|---|---|---|
| 1 | 0.0 ± 0.0 n = 2 | 0.0 ± 0.0 n = 2 |
| 2 | 0.0 ± 0.0 n = 2 | 1.0 ± 0.5 n = 2 |
| 3 | 0.0 ± 0.0 n = 2 | 1.8 ± 1.3 n = 2 |
| 4 | 0.0 ± 0.0 n = 2 | 2.8 ± 0.3 n = 2 |
| 5 | 0.0 ± 0.0 n = 2 | 2.8 ± 0.3 n = 2 |
| 6 | 0.0 ± 0.0 n = 2 | 3.0 ± 0.0 n = 2 |

TABLE 2

Effect of Mechanical Flexing of Copolymer-Incorporated Pericardial Valves on Calcification Of Tissue Implanted in Growing Rabbits

| TREATMENT | Implant Time (Weeks) | |
|---|---|---|
| | 3 | 6 |
| Acrylamide-Ethyl Methacrylate (Flexed) | 0.07 ± 0.02 n = 6 | 0.08 ± 0.05 |
| Acrylamide-Ethyl Methacrylate (Nonflexed) | 0.07 ± 0.02 n = 8 | 0.34 ± 0.25 |
| Ethyl Methacrylate-Butyl Methacrylate (Flexed) | 0.07 ± 0.01 n = 8 | 0.21 ± 0.14 |
| Ethyl Methacrylate-Butyl Methacrylate (Nonflexed) | 0.06 ± 0.03 n = 6 | 0.08 ± 0.04 |
| Ethyl Methacrylate-Hydroxyethyl Methacrylate (Flexed) | 0.06 ± 0.02 n = 7 | 0.14 ± 0.10 |
| Ethyl Methacrylate-Hydroxyethyl Methacrylate (Nonflexed) | 0.05 ± 0.02 n = 7 | 0.12 ± 0.10 |
| Butyl Methacrylate-Hydroxyethyl Methacrylate (Flexed) | 0.06 ± 0.02 n = 6 | 0.13 ± 0.09 |
| Butyl Methacrylate-Hydroxyethyl Methacrylate (Nonflexed) | 0.06 ± 0.01 n = 7 | 0.11 ± 0.09 |
| Control | 0.13 ± 0.05 n = 10 | 2.10 ± 0.51 |

What is claimed is:

1. A process for treating animal biological tissue prior to implantation into an animal to increase the durability of the tissue and to reduce calcification of said tissue after implantation comprising the steps of:
   (a) fixing said tissue under tissue-fixing conditions;
   (b) contacting said fixed tissue with a first solution of one or more monomers capable of further polymerization under conditions sufficient to covalently bond said monomer(s) to the tissue; and
   (c) contacting said tissue with a second solution containing one or more monomers or oligomers under polymerization conditions such that the monomers or oligomers in the second solution polymerize with said covalently bound first monomer(s) to form an elastomeric polymer in an amount effective in reducing calcification of said tissue after implantation.

2. The process of claim 1 wherein said second monomer or oligomer solution comprises two or more different monomers, at least one of which is an ester of acrylic acid or of methacrylic acid.

3. The process of claim 2 wherein the ester(s) of acrylic or methacrylic acid is present in amounts of from about 30 to about 100 weight percent of the total weight of the monomers or oligomers in the second monomer or oligomer solution.

4. The process of claim 3 wherein the ester(s) of acrylic or methacrylic acid is present in amounts of from 50 to 100 weight percent of the total weight of the monomers or oligomers in the second monomer or oligomer solution.

5. The process of claim 2 wherein the ester(s) of acrylic or methacrylic acid is selected from the group consisting of methyacrylate, methyl methyacrylate, ethyl acrylate, ethyl methacrylate, propyl acrylate, propyl methacrylate, butyl acrylate, butyl methacrylate, hydroxy ethyl acrylate, hydroxy ethyl methacrylate, hydroxy propyl acrylate, hydroxy propyl methacrylate, hydroxy butyl acrylate, hydroxy butyl methacrylate, acrylic acid glycerine ester, methacrylic acid glycerine ester, acrylic acid erythritol ester, methacrylic acid erythritol ester, acrylic acid pentaerythritol ester, and methacrylic acid pentaerythritol ester.

6. The process of claim 1 further comprising the step of removing non-covalently bound monomer from said tissue between steps (b) and (c).

7. The process of claims 1 or 2 wherein said first monomer is chosen from acrylic acid, methacrylic acid, acrylamide, methacrylamide, esters of acrylic acid, or esters of methacrylic acid.

8. The process of claim 1 wherein said second monomer solution comprises only one monomer species.

9. The process of claim 8 wherein the second monomer is an ester of methacrylic acid.

10. The process of claim 2 wherein said second monomer solution, in addition to said ester derivative(s) of acrylic or methacrylic acid, comprises acrylamide, acrylic acid, methacrylic acid, methacrylamide, or mixtures thereof.

11. The process of claim 2 wherein the monomer in said first monomer solution is acrylic acid or methacrylic acid, and said second monomer or oligomer solution comprises two or more esters of acrylic or methacrylic acid.

12. The process of claim 2 wherein the first monomer covalently bound to said tissue is acrylic acid, and the second monomer solution comprises a mixture of esters of acrylic or methacrylic acid, and acrylamide.

13. The process of claim 1 wherein the second monomer solution contains from about 0.1 to about 10.0 weight percent total of one or more monomers or oligomers.

14. The process of claim 3 wherein the second monomer solution contains from about 0.5 to about 6 weight percent total of one or more monomers or oligomers.

15. The process of claim 14 wherein the second monomer solution contains from about 0.5 to about 2.0 weight percent total of one or more monomers or oligomers.

16. The process of claim 1 wherein said second solution additionally comprises a cross-linking agent.

17. The process of claim 16 wherein said cross-linking agent is bisacrylamide.

18. The process of claim 1 wherein said second solution additionally comprises a free radical scavenger.

19. The process of claim 18 wherein said free radical scavenger is ferrous ammonium sulfate.

20. The process of claim 1 wherein said tissue is contacted with a free radical initiator between steps (b) and (c) in an amount sufficient to catalyze the polymerization of the covalently-bound first monomers with the monomers or oligomers in said second solution.

21. The process of claim 20 wherein said free radical initiator is an aqueous solution comprising ammonium persulfate and N,N,N',N'-tetramethylenediamine.

22. The process of claim 1 further comprising covalently binding a spacer to said fixed tissue between steps (a) and (b) so that the monomer(s) in said first solution is covalently bound to said tissue through the spacer.

23. The process of claim 22 wherein said spacer is a diamine compound.

24. The process of claim 23 wherein said diamine compound has the formula $R-(NH_2)_2$, wherein R is an aliphatic group having a straight, branched or cyclic chain, or an aromatic group.

25. The process of claim 24 wherein said diamine compound is ethylenediamine.

26. The process of claim 24 wherein said diamine is covalently bound to said fixed tissue in the presence of a carbodiimide.

27. The process of claim 1 wherein said biological tissue is a tendon, ligament, heart valve, dura mater, fascia lata, amnion or pericardium taken from a bovine, porcine, horse, sheep, kangaroo, rabbit, or human cadaver source.

28. The process of claim 1 wherein said tissue is fixed with glutaraldehyde.

29. A process for treating animal biological tissue prior to implantation in an animal to increase the durability of said tissue and to reduce calcification of said tissue after implantation comprising the steps of:
  (a) fixing said tissue under tissue-fixing conditions;
  (b) contacting said tissue with a first solution of a monomer capable of further polymerization for a time sufficient to impregnate said monomer in said tissue; and
  (c) contacting said tissue with a second monomer solution containing one or more monomers or oligomers, under polymerization conditions such that the monomers or oligomers in said second solution polymerize with said first monomer impregnated within said tissue to form an elastomeric polymer in an amount effective in reducing calcification of said tissue after implantation.

30. The process of claim 29 wherein said second monomer or oligomer solution comprises two or more different monomers at least one of which is an ester of acrylic acid or of methacrylic acid.

31. The process of claims 29 or 30 wherein said first monomer is acrylic acid or methacrylic acid.

32. The process of claim 30 wherein said second monomer solution contains, in addition to at least one ester of acrylic or methacrylic acid, monomers chosen from acrylamide, acrylic acid, methacrylic acid, or methacrylamide.

33. The process of claim 30 wherein said second monomer solution contains two or more esters of acrylic or methacrylic acid.

34. A method for reducing calcification of fixed animal biological tissue after implantation in an animal, wherein mitigation of calcification is maintained whether or not said tissue is subjected to flexing or stretching after implantation, comprising: covalently binding a monomer capable of further polymerization onto said biological tissue, and polymerizing one or more monomers or oligomers with said first monomer bound to said tissue prior to implantation to form an elastomeric polymer bound to said tissue in an amount effective to reduce calcification after implantation and increase the durability of the tissue.

35. Biological tissue having a reduced tendency toward calcification after implantation in an animal, including implantation in a position that subjects said tissue to stretching or flexing, said tissue having an elastomeric polymer incorporated therein according to the process of claim 1, 22 or 29.

* * * * *

UNITED STATES PATENT AND TRADEMARK OFFICE
CERTIFICATE OF CORRECTION

PATENT NO. : 4,770,665
DATED : September 13, 1988
INVENTOR(S) : Nashef

It is certified that error appears in the above-identified patent and that said Letters Patent is hereby corrected as shown below:

Col. 1, line 44, "glutaralde-hydetreated" should be --glutaraldehyde-treated--.

Col. 2, line 34, after "polymers" insert --.--.

Col. 7, line 41, after "preferred" insert --.--;

Col. 7, line 63, delete ",".

Col. 11, line 1, "foraldehyde" should be --formaldehyde--.

Col. 13, line 1, "3" should be --13--.

Col. 13, line 36, "24'" should be --23--.

Signed and Sealed this

Twenty-seventh Day of March, 1990

*Attest:*

JEFFREY M. SAMUELS

*Attesting Officer*  *Acting Commissioner of Patents and Trademarks*